US005655525A

United States Patent [19]
Orr

[11] Patent Number: 5,655,525
[45] Date of Patent: Aug. 12, 1997

[54] EMERGENCY BREATHING DEVICE IN COMBINATION WITH DECORATIVE DISPLAY

[76] Inventor: Rodney J. Orr, 3937 W. Maple, Wixom, Mich. 48393

[21] Appl. No.: 522,286

[22] PCT Filed: Aug. 17, 1995

[86] PCT No.: PCT/US95/10429

§ 371 Date: Apr. 17, 1996

§ 102(e) Date: Apr. 17, 1996

[87] PCT Pub. No.: WO96/04949

PCT Pub. Date: Feb. 22, 1996

Related U.S. Application Data

[63] Continuation-in-part of Ser. No. 291,719, Aug. 17, 1994.

[51] Int. Cl.$^6$ .............................. A62B 18/02; A62B 7/00; A62B 9/00; A61M 16/00
[52] U.S. Cl. .................. 128/205.25; 128/205.22; 128/206.21; 128/206.28; 128/205.23; 128/201.22; 128/202.22; 128/202.27
[58] Field of Search ........... 128/200.24, 201.22–201.26, 128/202.22, 202.27, 204.18, 204.29, 205.12, 205.23, 205.25, 205.27, 206.12, 206.21, 206.27, 206.28, 205.22

[56] References Cited

U.S. PATENT DOCUMENTS

| | | |
|---|---|---|
| 1,848,951 | 3/1932 | Haynes . |
| 2,177,204 | 10/1939 | Buzick et al. . |
| 2,262,040 | 11/1941 | Pell . |
| 2,550,954 | 5/1951 | Benedict . |
| 2,680,317 | 6/1954 | Lewis . |
| 2,831,607 | 4/1958 | Berndt . |
| 2,855,712 | 10/1958 | Diletto . |
| 3,483,887 | 12/1969 | Warncke et al. . |
| 4,078,561 | 3/1978 | Hanson . |
| 4,440,163 | 4/1984 | Spergel . |
| 4,440,164 | 4/1984 | Werjefelt . |
| 4,637,387 | 1/1987 | Hall . |
| 4,710,756 | 12/1987 | Thornburg et al. . |
| 4,726,365 | 2/1988 | Jablonski . |
| 4,840,171 | 6/1989 | Rohling et al. . |
| 4,905,684 | 3/1990 | Heffer . |
| 4,996,982 | 3/1991 | Williamson . |
| 5,113,854 | 5/1992 | Dosch et al. . |
| 5,239,989 | 8/1993 | Chen . |
| 5,243,972 | 9/1993 | Huang . |
| 5,301,665 | 4/1994 | Jumpertz et al. . |
| 5,429,125 | 7/1995 | Wagner et al. . |

FOREIGN PATENT DOCUMENTS 2030869  4/1980  United Kingdom .

OTHER PUBLICATIONS

EVAC–U8 Emergency Escape Smoke Hood, The Sportsman's Guide catalogue, Aug. 1995, p. 40.
E.D. Bullard Company ad and Pro–Tech Respirators, Inc. ad, Thomas Register 1990, p. 20536.
Racal Health & Safety, Inc. ad, Thomas Register 1990, p. 20537.
Industrial Safety & Security Co. ad, Thomas Register 1990, p. 20539.
North Safety Equipment ad, Glendale Protective Technologies ad, and MSA ad, Thomas Register 1990, p. 20540.
Primatene Mist instruction pamphlet, Whitehall Laboratories, no year of publication given.

*Primary Examiner*—Kimberly L. Asher
*Attorney, Agent, or Firm*—Weiner, Carrier & Burt, P.C.; William F. Esser; Irving M. Weiner

[57] ABSTRACT

An emergency breathing apparatus comprising an enclosure, a smoke detector and an alarm device operably disposed in the enclosure, and one or more emergency breathing devices having combination flashlight/beepers devices connected thereto also removably stored in the enclosure.

5 Claims, 7 Drawing Sheets

EMERGENCY BREATHING DEVICE IN COMBINATION WITH DECORATIVE DISPLAY

This application is a continuation-in-part of U.S. patent application Ser. No. 08/291,719 filed Aug. 17, 1994.

BACKGROUND OF THE INVENTION

1. Field of the Invention

This invention pertains to a device for providing air in emergency situations, and particularly to a device which includes a decorative and/or functional feature so that the device can be attractively located in any environment.

2. Description of the Relevant Art

Hall U.S. Pat. No. 4,637,387 discloses a breathing apparatus having a mask operatively connected to a cylinder. Hall fails to disclose a breathing apparatus having a mouthpiece member for providing airflow to the user thereof, and a decorative front portion for aesthetically-pleasing display thereof in a variety of locations.

Williamson U.S. Pat. No. 4,996,982 discloses a portable emergency breathing apparatus having a mouthpiece, regulator, and air storage container, but fails to disclose a breathing apparatus having a decorative front portion for open, inconspicuous display thereof in a variety of settings, and means for indicating its location in darkness.

Spergel U.S. Pat. No. 4,440,163 discloses an emergency breathing apparatus which attaches to an air cylinder, but fails to disclose an emergency breathing apparatus having a decorative front portion suitable for tactful display in a variety of settings; and means for illuminating the device in darkness.

Hanson U.S. Pat. No. 4,078,561 discloses a helmet having an air supply container attached thereto. Hanson fails to disclose an emergency breathing apparatus which is adapted to be conveniently yet inconspicuously displayed in a variety of settings and which includes a visual indicator for easily locating the device in darkness.

Huang U.S. Pat. No. 5,243,972 discloses a portable mask which cooperates with an oxygen tank for supplying oxygen thereto, but fails to disclose a breathing device which doubles at a home decoration when not in use, including a visual indicator for quickly identifying its location in darkness.

There are known portable aerosol inhalers which provide doses of pressurized liquid medicine, such a Primatene® Mist Asthma Inhaler. Such devices fail to provide air or oxygen, are not suited as a home decoration when not in use as a medicinal device, and do not include means for indicating its location.

SUMMARY OF THE INVENTION

The terms "air" and "gas" as used herein are intended to mean any substance which can be safely breathed by a human being, including, but not limited to oxygen, air oxygen-rich air, purified air, filtered air, and noxious or smoke-filled air from which noxious substances and/or smoke have been substantially removed.

The invention provides a device being a simple and effective means for supplying air or oxygen in emergency situations, and being usable as a home-like decoration when not used as a breathing device.

A first embodiment provides a breathing apparatus for emergency situations, including a storage container having air or oxygen under pressure; a mouthpiece which is connected to the air container; an actuator which cooperates with the air container and the mouthpiece to selectively permit fluid communication therebetween; a decorative front surface for allowing the device to be conveniently located in a wide variety of settings, and audio and visual elements for easy accessibility of the device in a dark or smoke-filled environment.

In an emergency, the mouthpiece is inserted into the user's mouth, and air is discharged from the pressurized air container by activating the actuator. The device is preferably, but not necessarily, held in place solely by the mouthpiece, thereby leaving the hands substantially free for other emergency-related acts. The activation of airflow from the device is initiated by finger or mouth movement of the actuator. Air or oxygen is discharged from the container in a substantially continuous flow, or in bursts having predetermined duration and/or frequency.

When not in use in an emergency, the device is preferably decoratively situated in virtually any setting, by resting the device on a horizontal surface or by suspending it along a vertical surface so that its decorative front portion is in view. In one embodiment, the device slidably receives a picture or photograph for display. The device preferably includes audio and visual indicating means for quickly locating the device in a dark or smoke-filled environment, as well as guiding rescue personnel to a user in need.

When the pressure level within the container is low, the container may be refilled or optionally replaced by removing it from the actuator and mouthpiece assembly.

It is an object of the invention to provide an emergency breathing apparatus which is simple in design and inexpensive to manufacture.

Another object is to provide such an apparatus having means for discharging air or oxygen from a storage container simply and quickly without substantial manipulation thereof by the user's hands.

Another object is to provide a breathing apparatus having an aesthetically pleasing exterior which is easily accessible.

Another object is to provide a breathing apparatus having audio and visual means for indicating the location thereof in darkness.

Other objects, advantages and salient features of the present invention will become apparent from the following detailed description, which, when taken in conjunction with the annexed drawings, discloses preferred embodiments of the present invention.

DETAILED DESCRIPTION OF THE INVENTION

FIGS. 1–4 shows an emergency breathing apparatus 60 including container 1, mouthpiece 2, actuator 3, and front section 4. The apparatus is preferably, but not necessarily, constructed from sturdy yet lightweight materials, such as molded plastic, aluminum, fiberglass, or a combination thereof. Container 1, mouthpiece 2, actuator 3, and front section 4 may preferably, but not necessarily, be integrally connected together to form a unitary member.

Container 1 is preferably, but not necessarily, constructed to effectively store air, oxygen, oxygen-rich air, or filtered air, under pressure. Container 1 has a port assembly actuator 3 for charging and/or discharging the container. Such port assembly preferably but not necessarily includes a sealing valve member 11 which is positioned within the port assembly to selectively control the opening of container 1.

Alternatively, container 1 may include means 12 for filtering (smoke or other undesirable substances) from the surrounding air, and for providing purified air to the user. Inlet device 13 permits the ambient air to flow into means 12 where the air is filtered and purified.

As a further alternative, the container 1 may include means 12 which generates oxygen and/or oxygen-rich air by way of a chemical or a combined chemical plus physical reaction. Oxygen and/or oxygen-rich air can be obtained by various known reactions. Such reaction may be activated by the user pressing a reaction-activation device 14.

Figure 1:
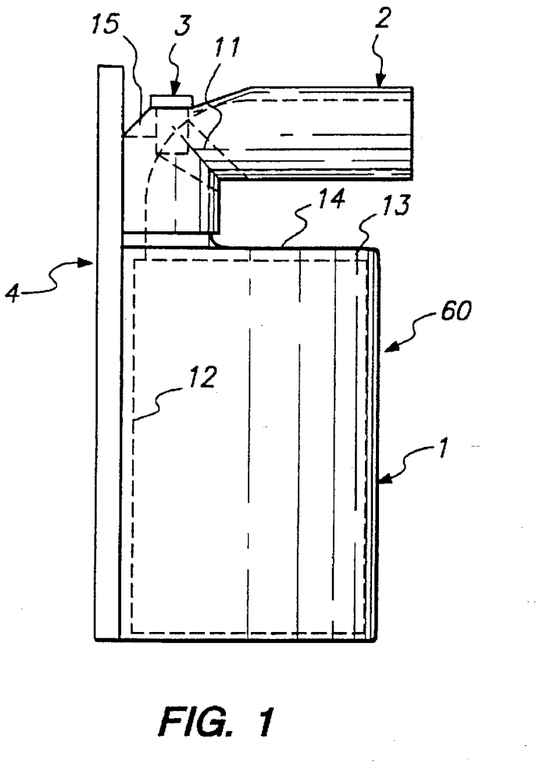
FIG. 1 is a side elevational view of an embodiment of the invention.
Figure 2:
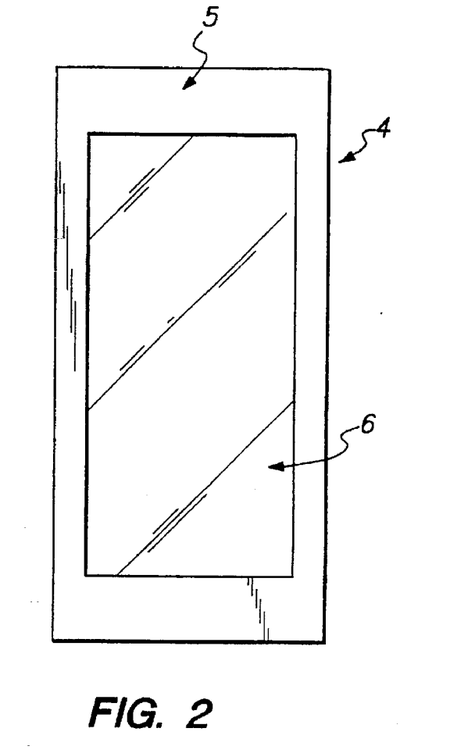
FIG. 2 is a front elevational view thereof.
Figure 3:
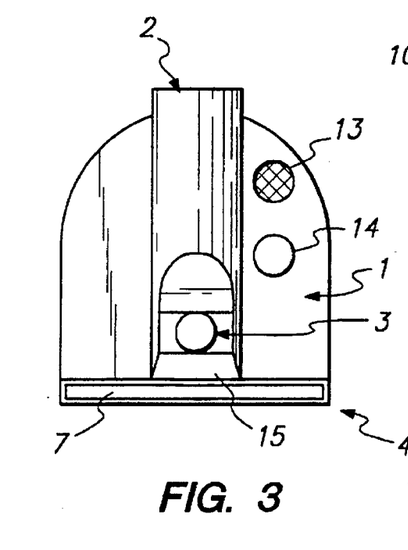
FIG. 3 is a top elevational view thereof.
Figure 4:
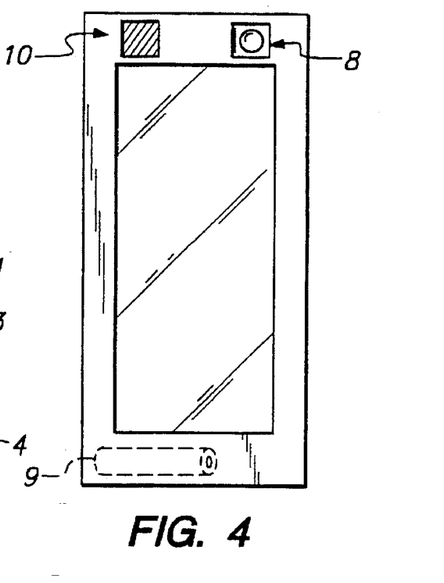
FIG. 4 is a front elevational view of another embodiment of the invention.

The invention includes mouthpiece 2 and actuator 3, as shown in FIGS. 1 and 3. Mouthpiece 2 preferably but not necessarily comprises a substantially tubular portion which extends outwardly from container 1, having an opening at end thereof for insertion into the user's mouth. A second end of mouthpiece 2 operatively attaches over the mouth portion of container 1. Alternatively, a mask is operatively attached to container 1 and adapted to fit over a user's nose and mouth region.

Actuator 3 preferably but not necessarily may include means for selectively discharging pressurized air, oxygen, oxygen-rich air, or filtered air from container 1 without requiring substantial manipulation of the breathing device by the user's hands. Such discharging means includes means, connected to the sealing valve member of container 1, for selectively switching the sealing valve member between a first position in which the sealing valve substantially seals the opening of container 1, and a second position in which the sealing valve allows air to pass therethrough. Such switching means, which toggles the sealing valve member of container 1 between the first (closed) and second (open) positions, is preferably activated by hand or mouth movements of the user, such as by activating switch by finger applied pressure, or by blowing into or biting into mouthpiece 2. In this way, the only manual manipulation of the breathing device necessary to discharge of gas therefrom is by a quick and simple act to initiate the discharge.

When the sealing valve member of container 1 is switched into the open position, gas is preferably discharged from container 1 having a predetermined, substantially continuous flow which provides a sufficient air supply to the user without prematurely discharging the entire contents thereof. The size of container 1 and the relationship between the sealing valve and the opening thereof is such that an adequate supply of air or oxygen is supplied to mouthpiece 2 for a period of several minutes or longer.

The invention may be used in a variety of settings, such as in hotels, motels, airplanes, trains, buses, ships, single family dwellings, or high-rise office buildings. Because the nature of each setting requires the breathing device to provide safe breathable air for different durations, container 1 may have a variety of sizes.

Air or oxygen is preferably, but not necessarily, substantially continuously discharged from container 1 until the pressure difference between container 1 and the atmosphere is substantially the same; or until the user switches the sealing valve member from the open to the closed position via finger or mouth control of actuator 3; or until the filtering means ceases to function; or until said reaction is no longer capable of occurring.

Alternatively, the structural relationship between actuator 3 and sealing valve member may be such that air is discharged from container 1 in bursts having predetermined duration. The invention may include a battery-operated electronic means 15, connected to the sealing valve member, for controlling the duration of each burst and the time period therebetween for prolonged yet safe operation. Such electronic control means 15 preferably but not necessarily includes a pre-programmed or programmable timer for providing electrical control signals to an electromechanical sealing valve member. In this instance, the activation of the breathing apparatus is initiated and concluded simply by operating a switch located along the side thereof.

The invention may additionally include means for removably attaching actuator 3 and mouthpiece 2 to container 1. Such removable attaching means allows container 1 to be either refilled or disposed of and replaced when the pressure level therein is low. In a preferred embodiment, the actuator 3 and mouthpiece 2 slide over the mouth portion of container 1. In an alteratively embodiment, mouthpiece 2 threadingly engages with container 1.

The invention may also include a decorative front portion which serves as an aesthetically-pleasing home-like decoration so that the invention can be conveniently located in a variety of settings. As shown in FIGS. 1–4, front portion 4 preferably but not necessarily comprises a picture frame having border member 5 and transparent portion 6. Alternatively, front portion 4 may include or comprise another decoration.

The frame portion of front portion 4 may have any of a variety of shapes, such as rectangular or oval-shaped, but preferably the frame is sized so that container 1, mouthpiece 2, and actuator 3 are substantially unobservable when the device is viewed along a front view thereof. The decorative front portion of the device having such a frame size relative to container 1, mouthpiece 2, and actuator 3 allows the device to be located in virtually any setting fashionably and tastefully, thus improving its availability and accessibility in times of an emergency by openly maintaining the breathing device is areas near people. Front portion 4 of the breathing apparatus preferably but not necessarily includes means for slidably receiving a picture or photograph. As shown in FIG. 3, front portion 4 includes elongated slot 7 defined longitudinally along front portion 4. The length and width of slot 7 are preferably but not necessarily substantially comparable to the corresponding dimensions of front portion 4, and the depth of slot 7 is preferably sized to receive a photograph or picture in a substantially fixed position therein.

Front portion 4, mouthpiece 2, and actuator 3 are preferably but not necessarily integrally formed as a unitary member, such as being formed from molded plastic.

The invention includes means for visually indicating its location in a dark or smoke-filled environment. Such visual indicating means preferably but not necessarily comprises an outer portion of the apparatus being constructed from luminescent material so as to substantially flow in the dark following exposure to a light source. The luminescent portion of the breathing apparatus preferably includes one or more of border 5 of front portion 4, container 1, or mouthpiece 2.

Alternatively, the visual indicating means of the breathing apparatus may include light bulb 8, which is positioned along border 5 of front portion 4 (FIG. 4), or along a side portion of actuator 3. Light bulb 8 is preferably selectively activated by a switch located along a side portion of container 1. For light bulb 8 to function in substantially any location, light bulb 8 is preferably powered by a battery 9, which is disposed along an under portion or back portion of the breathing apparatus. In another embodiment, the breathing apparatus includes electrical means connected to light bulb 8 for selectively inserting within an electrical outlet to provide power to light bulb 8, and for suspending the breathing apparatus therealong.

The apparatus may include means for generating a sound in the event of an emergency. The sound generating means preferably but not necessarily may comprise an electronic sound generator 10 which selectively automatically generates a relatively loud series of sounds, such as a series of beeping sounds. Sound generator 10 is preferably but not necessarily activated by a switch and powered by a battery 9. Upon activation of the sound generating means by the user, firepersons or other rescue personnel can more quickly and easily locate the user of the device. If the breathing device becomes separated from the user, the user can quickly find it due to its sound generating means.

The device preferably includes a strap which is attached to the device and is adapted to facilitate the suspension thereof when the device is in use as a emergency breathing device. The strap is preferably but not necessarily elastic so that it aids in supporting the device in the breathing position for substantially any sized user. The strap allow the user to easily locate the breathing device in the event mouthpiece 2 of the device becomes dislodged from the user's mouth.

In use as a breathing device in an emergency, the open end of mouthpiece 2 is inserted into the user's mouth. Next, actuator 3 is activated by a the user's finger or mouth, which initiates fluid communication between mouthpiece 2 and container 1 by switching the sealing valve member of container 1 into the open position. Such establishment of fluid communication causes the gas to be discharged from container 1 into mouthpiece 2, thus discharging a safe breathable gas from container 1 into the user's respiratory system.

In one embodiment, air is discharged substantially continuously, whereas in another embodiment the gas is discharged in a controlled series of periodic bursts. When it is no longer necessary to discharge gas from the breathing apparatus, actuator 3 is deactivated, thereby switching the sealing valve member of container 1 into the closed or sealed position. Sound generating means 10 is selectively activated to produce a series of audio signals for indicating its location thereof in adverse conditions.

When not actively used in an emergency, the breathing device can be located in a wide variety of settings by placing a photograph or picture within slot 7 and either resting the device on a horizontal surface, hanging the device along a wall, or plugging an electrical receptacle portion thereof in an electrical outlet.

Figure 5:
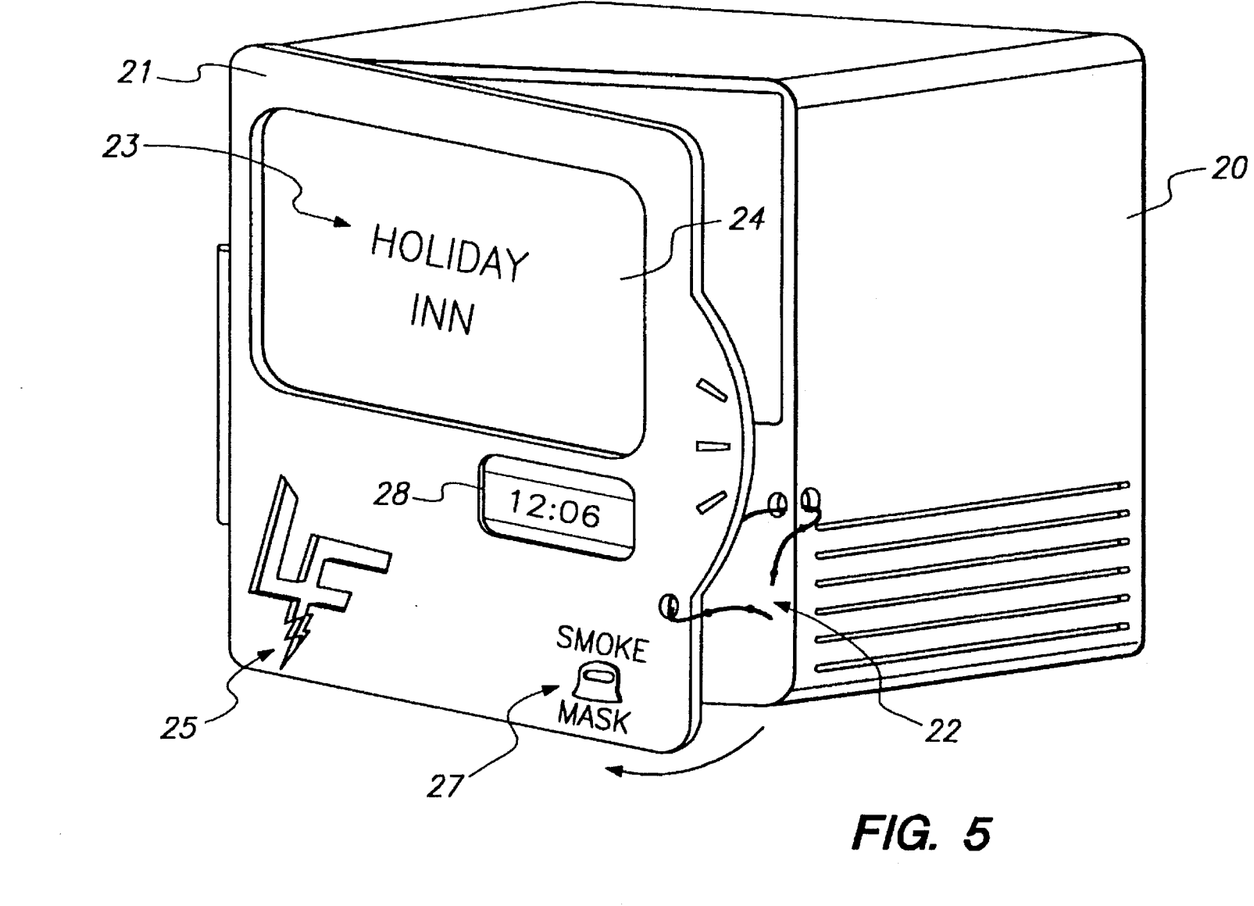
FIG. 5 is a front perspective view of another embodiment.

FIG. 5 shows another embodiment comprising a housing 20 having a door plate 21 hingedly affixed thereto. The door plate 21 is provided with a tamper proof seal 22 which is easily broken by the user.

The door plate 21 is provided with a receptacle 23 for a photo 24, such as a hotel logo. The door plate 21 may also be provided with a cut-out front logo 25 which is illuminated from behind by way of LEDs 26 to show the name of the manufacturer by its logo 25. The door plate 21 may also be provided with a "Smoke Mask" symbol 27 which is also illuminated, as well as a clock 28.

Figure 6:
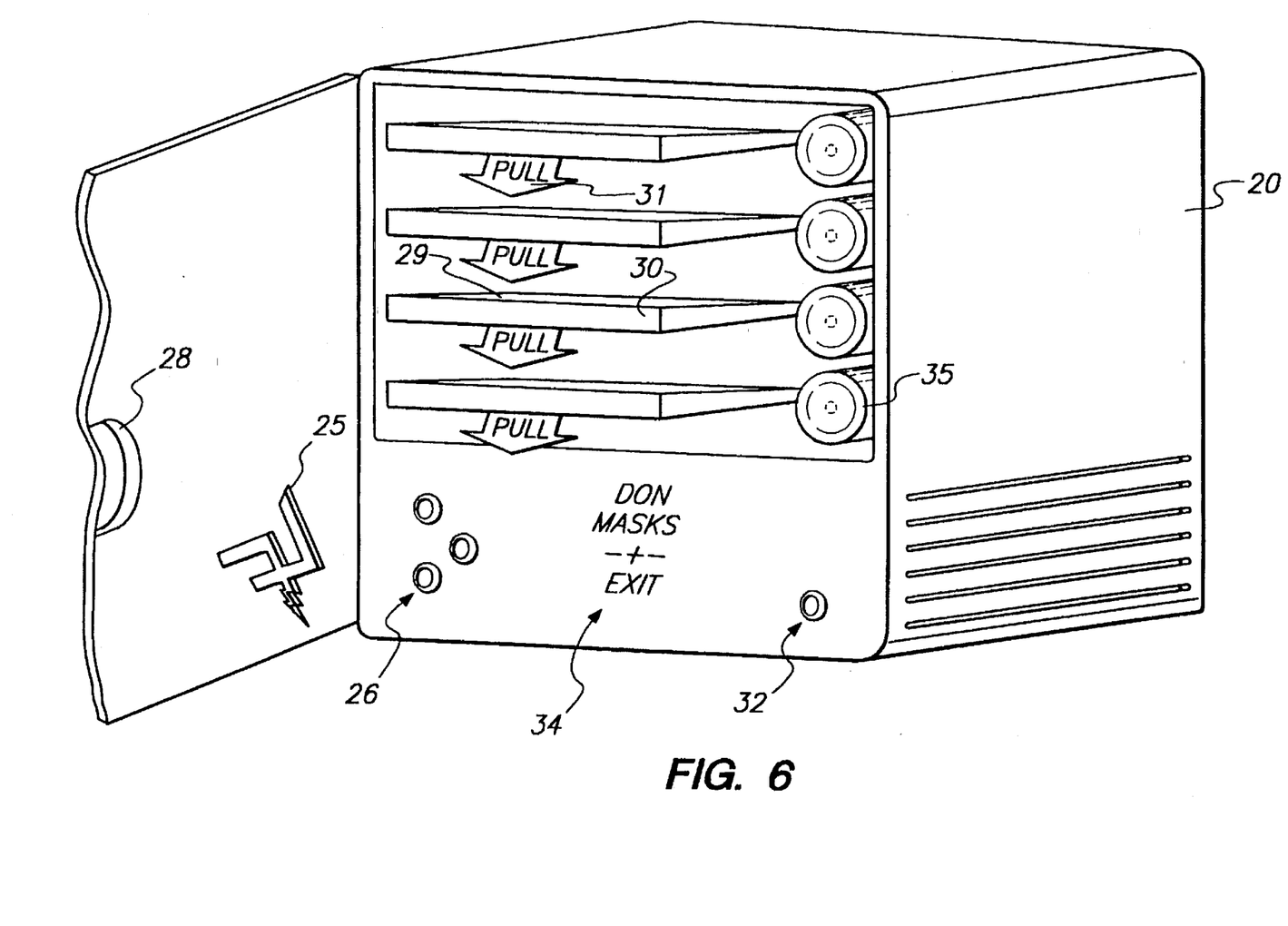
FIG. 6 shows the FIG. 5 embodiment with the front door swung open.

FIG. 6 shows the FIG. 5 embodiment with the door plate 21 swung open to reveal four emergency breathing masks 29 in sealed pouches 30 with pull tabs 31. These masks 29 are capable of filtering and purifying smoke-filled air to provide a safe, breathable substance to the user.

FIG. 6 also shows the LEDs 26 for the front logo as well as the LEDs 32 for the "Smoke Mask" symbol 27. The unit may be provided a message 34 such as "Don Masks" and "Exit", which message 34 can be illuminated through the wall by internal LEDs. The apparatus may be located near an exit door, but need not necessarily be placed there.

Optionally, the enclosure 20 may also contain a plurality of flashlight/beeper devices 35 which when turned "ON" will illuminate as well as send out an audible signal. Optionally, such flashlight/beeper devices 35 may be affixed to or be unitary with associated masks 29.

Figure 7:
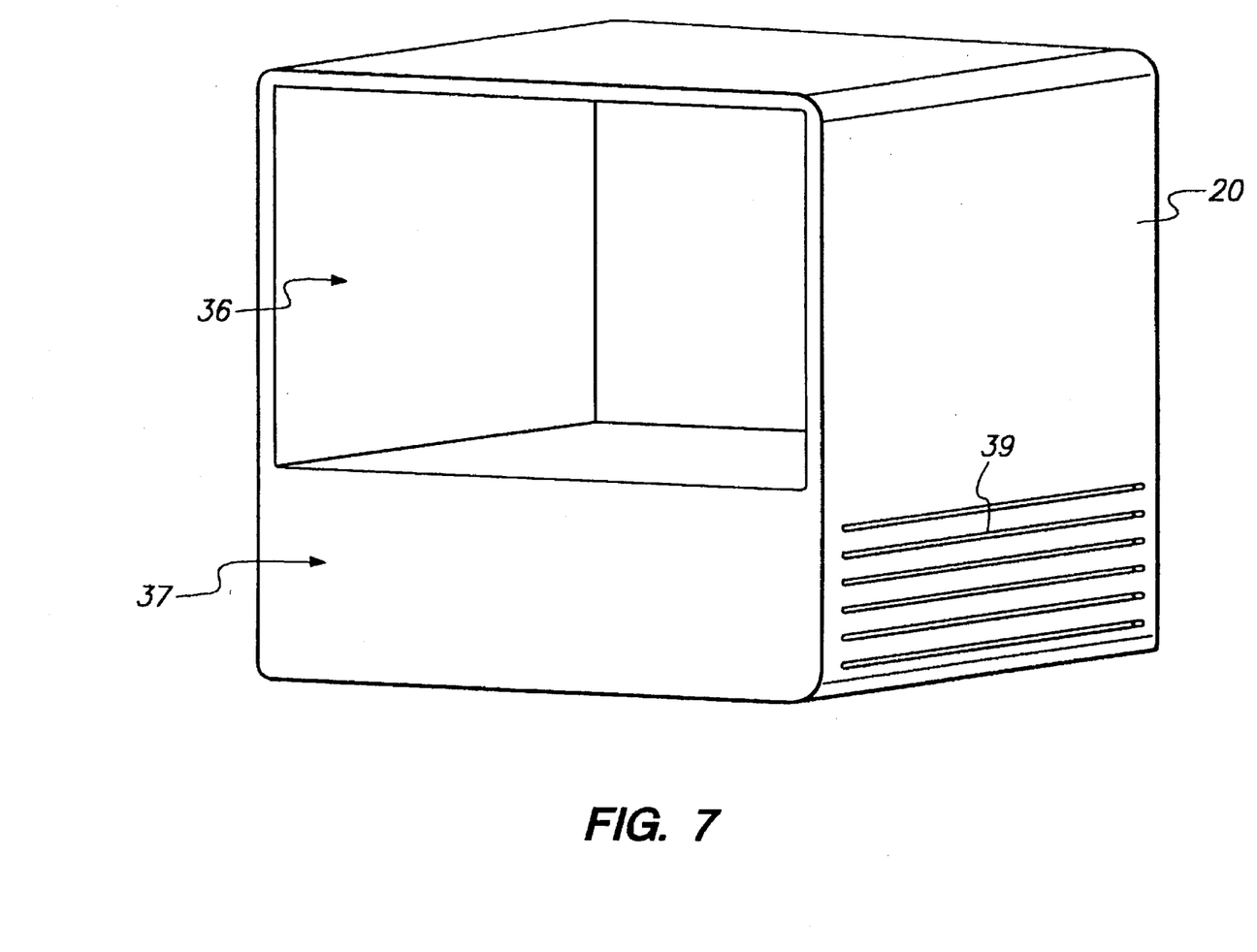
FIG. 7 shows the FIG. 5 embodiment with the door removed.

FIG. 7 shows the enclosure 20 with the door 21 removed to display the compartment 36 within which the mask 29/pouches 30 may be disposed with or without flashlight/beeper devices 35. There is also shown in FIG. 7 the compartment 37 for the detector/alarm electronics.

Figure 8:
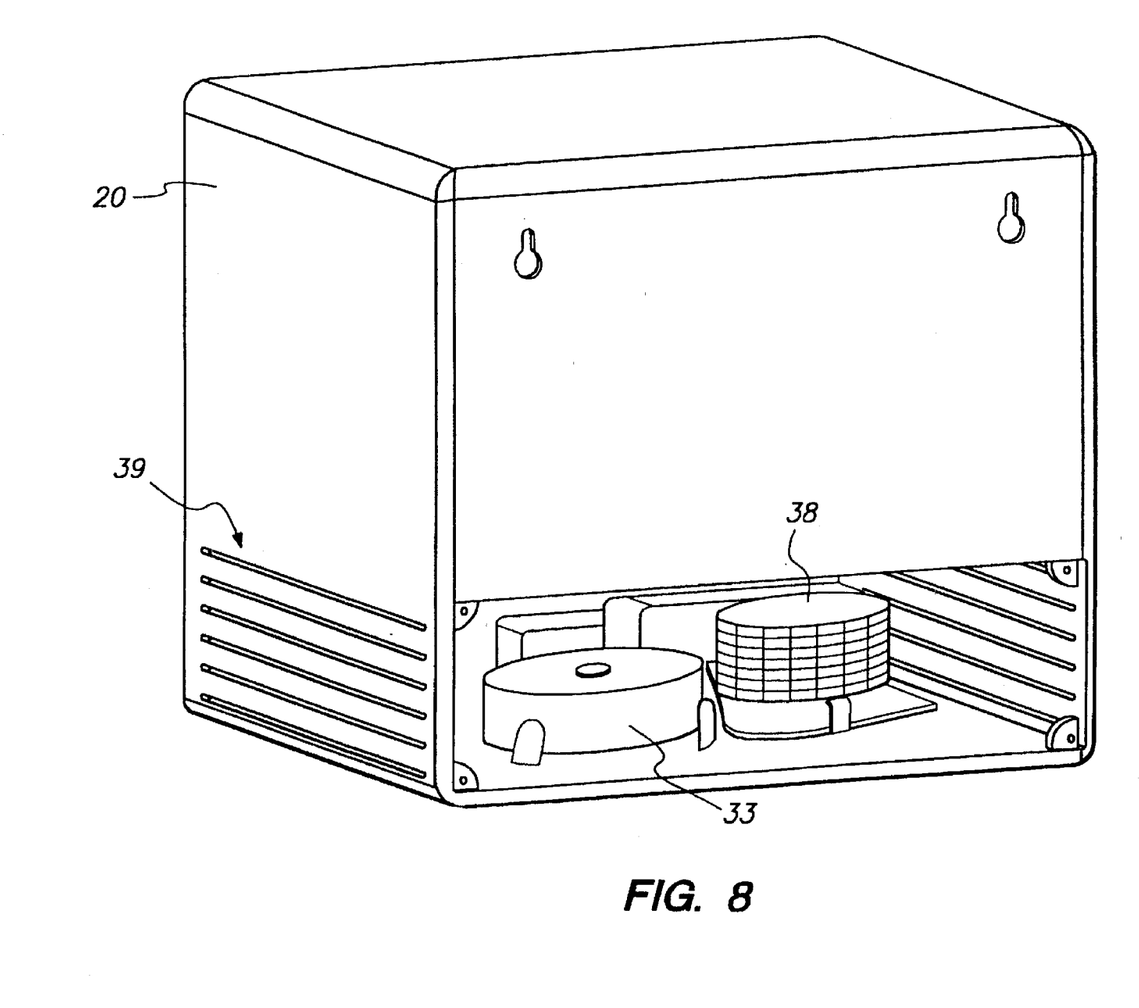
FIG. 8 shows a back view of the FIG. 5 embodiment.

FIG. 8 shows the detector/alarm electronics with the smoke detector 38 and alarm circuitry 33 energized by appropriate electrical batteries. Alternatively, the power may be supplied by a line cord which is plugged in. FIG. 8 also shows the vents 39 which are useful in the smoke detection process.

Figure 9:
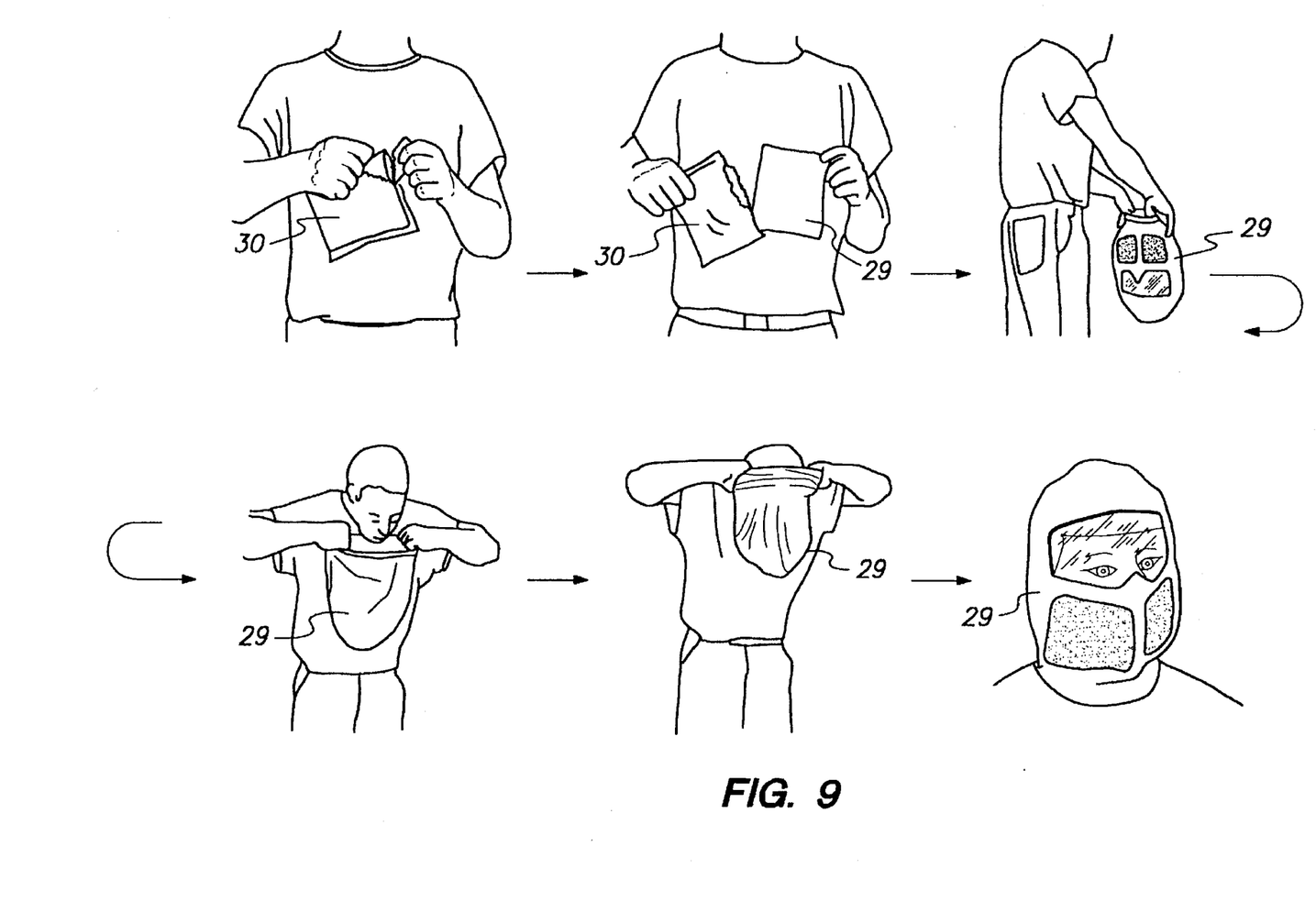
FIG. 9 is a composite instructional drawing showing the manner of extracting and using the air-purifying masks shown in FIG. 6.

FIG. 9 illustrates a sequence of steps for opening, extracting and using the masks 29 which are preferably kept in sealed pouches 30. For the sake of simplicity and understanding, FIG. 9 is illustrated without a flashlight/beeper device 35 affixed to the mask 29.

As an alternative to the masks 29 described above, there may be used a plurality of the devices 60 described hereinabove in connection with FIGS. 1–4.

Figure 10:
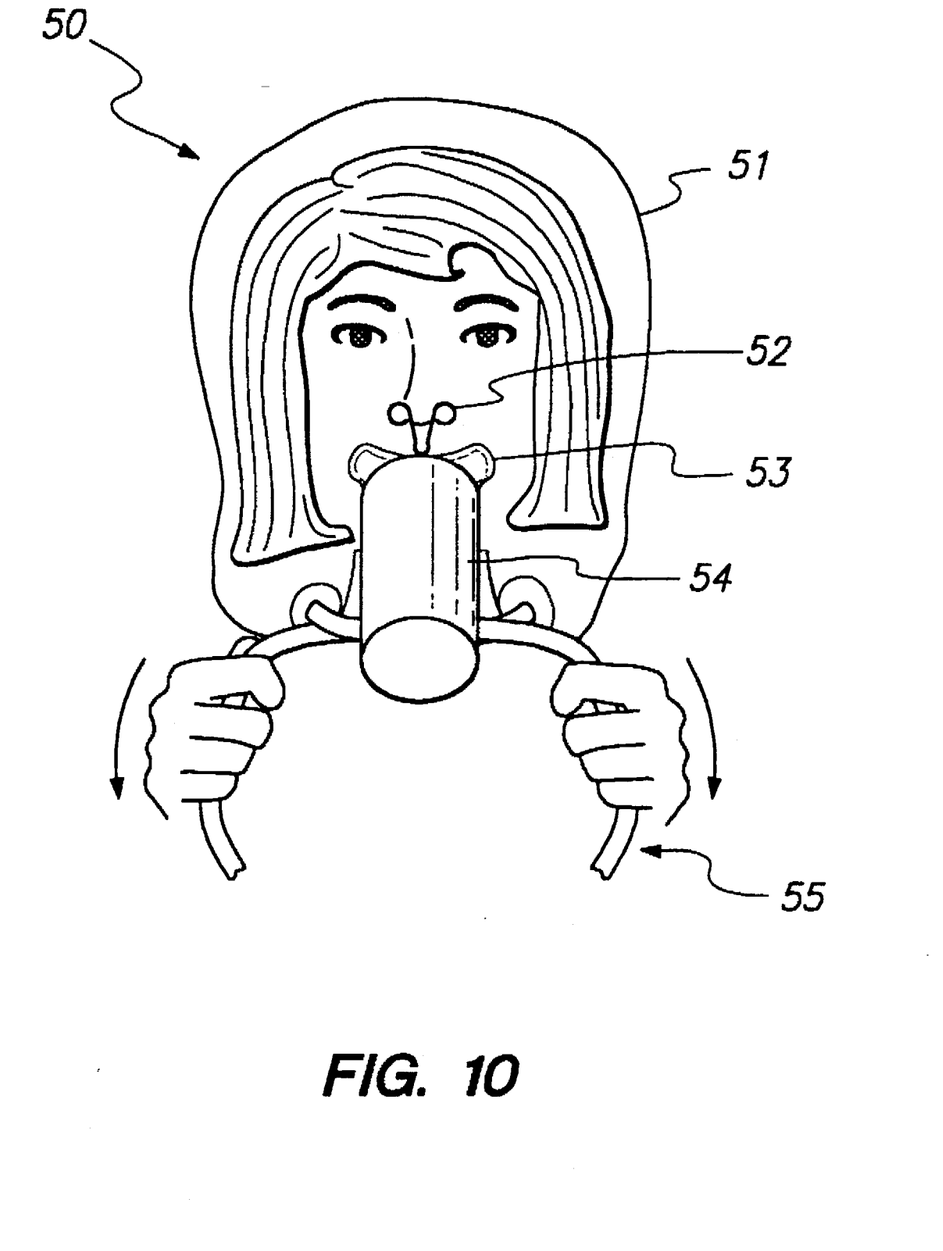
FIG. 10 shows a canister alternative to the mask device shown in FIG. 9.

As a further alternative to the masks 29 discussed hereinabove, there may be used a plurality of the devices 50 shown in FIG. 10. FIG. 10 shows a device 50 having a hood 51, a nose clip 52, a mouthpiece 53, a canister or filter casing 54, and draw strings 55. These components may optionally be heat resistant to levels beyond which the human body can withstand. The FIG. 10 device 50 supplies filtered or purified air to the user.

Although there have been described what are at present considered to be preferred embodiments of the present invention, it will be understood that the invention can be embodied in other specific forms without departing from the spirit or essential characteristic thereof.

The described embodiments are, therefore, to be considered in all aspects as illustrative, and not restrictive. The scope of the invention is indicated by the appended claims rather than by the foregoing description.

I claim:

1. An emergency breathing apparatus, comprising:
   an enclosure;
   a smoke detector and an alarm device operably disposed in said enclosure;

one or more emergency breathing devices removably stored in said enclosure;

one or more combination flashlight/beeper devices removably stored in said enclosure; and each said combination flashlight/beeper device is connected to an associated one of said emergency breathing devices.

2. An apparatus according to claim 1, wherein:

each said emergency breathing device includes means for generating oxygen and/or oxygen-rich air by way of a chemical or a combined chemical/physical reaction.

3. An apparatus according to claim 1, wherein:

each said emergency breathing device includes means for removing noxious substances including smoke from surrounding air to produce a safe breathable substance.

4. An apparatus according to claim 1, wherein:

each of said one or more emergency breathing devices includes a hood member, a nose clip, and a mouthpiece member.

5. An apparatus according to claim 1, wherein:

each of said one or more emergency breathing devices includes a hood member.

* * * * *